US012773524B2

(12) United States Patent
Gavalis et al.

(10) Patent No.: US 12,773,524 B2
(45) Date of Patent: Oct. 27, 2026

(54) MEDICAL SYSTEMS, DEVICES, AND RELATED METHODS

(71) Applicant: Boston Scientific Scimed, Inc., Maple Grove, MN (US)

(72) Inventors: Robb M. Gavalis, Westborough, MA (US); Jessica L. Powers, Boston, MA (US); Shannon S. Kenwood, Milford, MA (US); Gregory T. Hughes, Hanson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1130 days.

(21) Appl. No.: 17/663,534

(22) Filed: May 16, 2022

(65) Prior Publication Data

US 2022/0362511 A1 Nov. 17, 2022

Related U.S. Application Data

(60) Provisional application No. 63/189,504, filed on May 17, 2021.

(51) Int. Cl.

*A61M 25/00* (2006.01)
*A61B 1/018* (2006.01)

(Continued)

(52) U.S. Cl.

CPC ......... *A61M 25/0041* (2013.01); *A61B 1/018* (2013.01); *A61B 17/22032* (2013.01);

(Continued)

(58) Field of Classification Search

CPC ........ A61B 17/22032; A61B 17/22054; A61B 2017/22084; A61B 2017/22082;

(Continued)

(56) References Cited

U.S. PATENT DOCUMENTS 4,295,464 A * 10/1981 Shihata .............. A61M 25/1011 604/908
5,152,277 A * 10/1992 Honda ............... A61B 1/00135 604/920

(Continued)

FOREIGN PATENT DOCUMENTS

EP 03395270 A1 10/2018
JP 2004-283289 A 10/2004

(Continued)

OTHER PUBLICATIONS

International Search Report and Written Opinion issued in International Application No. PCT/US2022/072344, issued Aug. 30, 2022 (14 pages).

*Primary Examiner* — Jason E Flick
*Assistant Examiner* — Isabella S North
(74) *Attorney, Agent, or Firm* — Bookoff McAndrews PLLC

(57) ABSTRACT

According to one aspect, a method for removing material from a body lumen is disclosed. The method may include positioning a first medical device within the body lumen; and expanding an expandable member at a distal portion of the first medical device from a retracted state to an expanded state. The expandable member may abut the body lumen in the expanded state. The method may further include providing fluid to a fluid lumen of the first medical device, wherein the fluid is deployed into the body lumen; applying an ultrasound signal to the first medical device from a second medical device; and moving the first medical device distally through the body lumen while the expandable member is in an expanded state, to remove material from the body lumen.

15 Claims, 5 Drawing Sheets

(51) Int. Cl.

| | |
|---|---|
| ***A61B 17/22*** | (2006.01) |
| ***A61F 2/04*** | (2013.01) |
| ***A61F 2/82*** | (2013.01) |
| ***A61F 2/966*** | (2013.01) |
| ***A61M 25/09*** | (2006.01) |
| ***A61M 25/10*** | (2013.01) |

(52) U.S. Cl.
CPC ................ *A61F 2/82* (2013.01); *A61F 2/966* (2013.01); *A61M 25/09041* (2013.01); *A61B 2017/22054* (2013.01); *A61F 2002/041* (2013.01); *A61M 2025/109* (2013.01)

(58) Field of Classification Search
CPC ........... A61B 2017/22062; A61B 2017/22038; A61B 1/00082; A61M 2025/109
See application file for complete search history.

(56) References Cited

U.S. PATENT DOCUMENTS

| | | | | |
|---|---|---|---|---|
| 5,868,698 | A | 2/1999 | Rowland et al. | |
| 9,314,589 | B2 * | 4/2016 | O'Day | A61M 25/007 |
| 9,839,543 | B2 * | 12/2017 | Ridgley | A61M 25/1011 |
| 10,172,634 | B1 * | 1/2019 | Horowitz | A61B 17/22032 |
| 2009/0143764 | A1 * | 6/2009 | Nelson | A61M 25/007 604/528 |
| 2012/0259215 | A1 * | 10/2012 | Gerrans | A61M 25/1011 604/509 |
| 2014/0243790 | A1 * | 8/2014 | Callaghan | A61M 1/3659 604/509 |
| 2018/0161552 | A1 * | 6/2018 | Larson | A61B 17/22 |

FOREIGN PATENT DOCUMENTS

| | | | | |
|---|---|---|---|---|
| JP | 2006-223341 A | | 8/2006 | |
| JP | 2012-200368 A | | 10/2012 | |
| JP | 2014-140465 A | | 8/2014 | |
| WO | WO-9505209 A1 | * | 2/1995 | A61B 17/12136 |
| WO | 1999036120 A1 | | 7/1999 | |
| WO | WO-0215802 A1 | * | 2/2002 | A61B 17/22 |
| WO | WO 2007/136599 A2 | | 11/2007 | |
| WO | WO 2012/099974 A2 | | 7/2012 | |
| WO | 2016031071 A1 | | 3/2016 | |
| WO | 2017111164 A1 | | 6/2017 | |
| WO | WO-2020069216 A1 | * | 4/2020 | A61B 17/320758 |
| WO | 2020175462 A1 | | 9/2020 | |
| WO | WO-2021085537 A1 | * | 5/2021 | A61M 25/10 |

* cited by examiner

MEDICAL SYSTEMS, DEVICES, AND RELATED METHODS

CROSS REFERENCE TO RELATED APPLICATION

This application claims priority to U.S. Provisional Application No. 63/189,504, filed May 17, 2021, the entirety of which is incorporated by reference herein.

TECHNICAL FIELD

Various aspects of this disclosure relate generally to manipulation of bodily material, including visualizing, flushing, cleaning, and otherwise manipulating bodily material. More specifically, at least certain embodiments of this disclosure relate to systems, devices, and related methods for performing endoscopic ultrasound procedures, among other aspects.

BACKGROUND

Technological developments have given users of medical systems, devices, and methods, the ability to conduct increasingly complex procedures on subjects. Diseases and other conditions of the gallbladder, pancreas, and bile ducts (e.g. pancreaticobiliary system) are associated with impaired quality of life, significant morbidity, and mortality. Tumors, injuries, leakages, obstructions, lesions, and other problems can occur in the pancreaticobiliary system that may lead to conditions such as biliary colic, cholecystitis, choledocholithiasis, choleithiasis, pancreatitis, pancreatic duct stone formations, chronic abdominal pain, and other problematic health conditions. In some cases, conditions of the pancreaticobiliary system may be associated with nutritional disorders, such as malnutrition, obesity, and high cholesterol.

Biliary stones are a condition that affects millions of patients each year. ERCP (endoscopic retrograde cholangiopancreatography) procedures are currently the standard of care, and while preferable to open surgery, come with their own disadvantages and risks. ERCP procedures typically require the use of sphincterotomy to gain access into the bile duct, which may lead to inflammation at the site or even pancreatitis. Fluoroscopy is commonly used to aid in visualization, which poses health risks and requires use of large, specialized equipment. Smaller stone fragments or biliary sludge may not be detected, despite being linked to about 20-40% of cases of acute pancreatitis.

There is a need for systems, devices, and methods that are designed for manipulating bodily material, particularly for use in treating the pancreaticobiliary system.

SUMMARY

Aspects of the disclosure relate to, among other things, systems, devices, and methods for treating the pancreaticobiliary system, among other aspects. Each of the aspects disclosed herein may include one or more of the features described in connection with any of the other disclosed aspects.

According to one aspect, a method for removing material from a body lumen is disclosed. The method may include positioning a first medical device within the body lumen; and expanding an expandable member at a distal portion of the first medical device from a retracted state to an expanded state. The expandable member may abut the body lumen in the expanded state. The method may further include providing fluid to a fluid lumen of the first medical device, wherein the fluid is deployed into the body lumen; applying an ultrasound signal to the first medical device from a second medical device; and moving the first medical device distally through the body lumen while the expandable member is in an expanded state, to remove material from the body lumen.

In other aspects, the method may include one or more of the following features. The fluid lumen may be fluidically coupled to a plurality of openings at the distal end of the first medical device, and at least one opening may be oval shaped and at least one opening may be circular shaped. The first medical device may include at least one echogenic feature. The method may further include positioning a guidewire within the body lumen; and moving the first medical device along the guidewire. The expandable member may be configured to expand radially-outward from a central longitudinal axis of the medical device. The first medical device may include a cap at a distal end of the first medical device, wherein the fluid lumen of the first medical device is fiducially connected to an interior channel of the cap, and wherein applying fluid to a fluid lumen of the first medical device causes the cap to rotate about a central longitudinal axis of the first medical device. The expandable member may be a first expandable member, the method may further include, after providing fluid to a fluid lumen of the first medical device, expanding a second expandable member at a distal portion of the first medical device from a retracted state to an expanded state, wherein the second expandable member abuts the body lumen in the expanded state and is positioned distal to the first expandable member.

In other aspects, the method may include one or more of the following features. The first expandable member may be angled relative to a central longitudinal axis of the medical device when in an expanded state, and the radially-outermost portion of the first expandable member may be distal to the radially-innermost portion of the first expandable member when in an expanded state. The second expandable member may contact the first expandable member when each of the first expandable member and the second expandable member is in an expanded state. A second medical device may be positioned outside of the body lumen. The expandable member may be a first expandable member coupled to a first shaft, and the method may further include expanding a second expandable member from a retracted state to an expanded state, wherein the second expandable member is coupled to a second shaft positioned within the first shaft; and moving the second expandable member distally relative to the first expandable member. Moving the second expandable member distally relative to the first expandable member may be at least partially caused by pressure from fluid within a space between the first expandable member and the second expandable member of the body lumen. The first expandable member and the second expandable member may each forms a seal with the body lumen. A distal opening of the fluid lumen is positioned between the first expandable member and the second expandable member. The body lumen may be a common bile duct of a patient, and positioning the first medical device may include entering the common bile duct via an opening made in the common bile duct.

In other aspects, a method for removing material from a body lumen of the pancreaticobiliary system may include positioning a first medical device within the body lumen; and expanding an expandable member at a distal portion of the first medical device from a retracted state to an expanded state. The first expandable member may abut the body lumen in the expanded state. The method may further include providing fluid to a fluid lumen of the first medical device to cause rotation of a cap at a distal end of the first medical device and disperse fluid radially-outward from the first medical device in a plurality of directions; and apply an ultrasound signal to the first medical device from a second medical device. In some aspects, the cap may include at least one echogenic feature and a fluid exit channel, and the fluid exit channel may extend to a radially-outermost portion of the cap, relative to a central longitudinal axis of the first medical device.

In other aspects, a medical device may include a shaft including a working channel and at least one fluid lumen; an expandable member at a distal portion of the shaft; and at least one echogenic feature positioned at the distal portion of the shaft. In some aspects, the expandable member may be a first expandable member and the shaft may be a first shaft, the device may further include a second shaft extending through the working channel and out of a distal end of the first shaft, the second shaft longitudinally movable relative to the first shaft; and a second expandable member positioned at a distal end of the second shaft. A distal opening of the at least one fluid lumen may be positioned between the first expandable member and the second expandable member. In some aspects, the device may further include a first fluid channel fluidically coupled to the first expandable member; and a second fluid channel fluidically coupled to the second expandable member. Transitioning the first expandable member from a retracted state to an expanded state may include supplying fluid from the first fluid channel to an interior portion of the first expandable member; and transitioning the second expandable member from a retracted state to an expanded state may include supplying fluid from the second fluid channel to an interior portion of the second expandable member.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

DETAILED DESCRIPTION

This disclosure is drawn to systems, devices, and methods for treating the pancreaticobiliary system, among other aspects. Though examples in this disclosure focus on the pancreaticobiliary system, and its various ducts/lumens, aspects of this disclosure can be applied to any other body lumen, including any lumen of the gastrointestinal system, urinary system, etc. Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The proximal and distal directions are labeled throughout the drawings with an arrow labeled "D" for the distal direction and an arrow labeled "P" for the proximal direction. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Embodiments of this disclosure may be used to visualize and move target bodily material in an endo-luminal space, or facilitate the process thereof. In particular, some embodiments include ultrasound visualization devices and tissue flushing catheter devices.

Endoscopic ultrasound procedures are performed with a specialized endoscope or other medical device that uses high frequency soundwaves to visualize nearby structures. One of the advantages of using endoscopic ultrasound is the ability to "see" through walls without having to gain access, and it is a safer alternative to fluoroscopy.

The catheter device may be delivered to target tissue through an endoscope working channel to the target tissue site via a guidewire. One or more fluid jets of the catheter device may propel fluid at bodily material to remove the material from a body lumen. An expandable portion of the catheter device may move the material through the body lumen to facilitate its removal. All or parts of the catheter device could be formed of any biocompatible material, such as a shape memory polymer, a polymer, metal, plastic, and/or a shape memory metal (such as nitinol), or any combination of materials.

Figure 1:
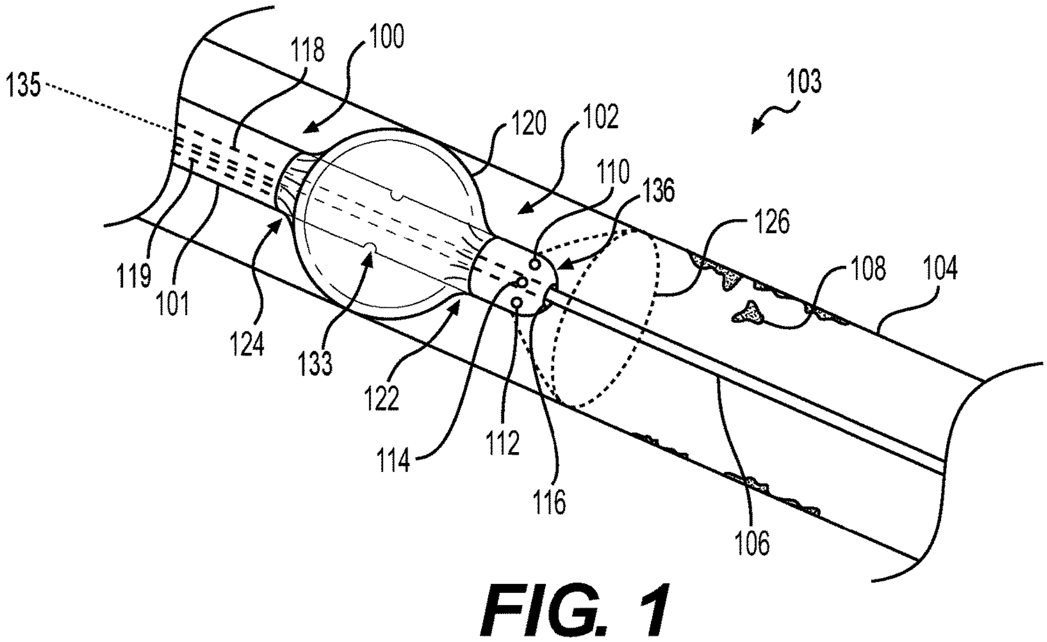
FIG. 1 is a perspective view of a distal end of an exemplary medical device system within a body lumen, according to aspects of this disclosure.

FIG. 1 shows a medical device system 103 within a body lumen 104 of a patient. Medical device system 103 may include a medical device 100 and a guidewire 106. In some examples, medical device system 103 may further include an endoscope 200 (shown in FIG. 2) or other medical device (e.g., ureteroscope, bronchoscope, duodenoscope, colonoscope, sheath, or the like for delivery of device 100 to a treatment site). Medical device 100 may be a catheter, and may include a longitudinal shaft 101, a distal end portion 102, and a proximal portion (not shown in FIG. 1). Proximal portion of medical device 100 may include one or more actuators, a handle, and/or one or more input ports for fluid, air, electrical, or other connections to medical device 100.

Shaft 101 may include a working channel 118 extending longitudinally through an interior portion of shaft 101 from distal end portion 102 to a proximal portion of shaft 101. Working channel 118 may be a cylindrical lumen configured to receive guidewire 106, and shaft 101 may be configured to move along guidewire 106 to a target area within the body of a patient. Working channel 118 is shown extending through a central portion of shaft 101 leading to a distal opening 116 at a central portion of distal end portion 102, however working channel 118 may extend longitudinally through any portion of shaft 101. Shaft 101 may include one or more echogenic features 133, such as a curved recess extending circumferentially around a central longitudinal axis 135 of shaft 101. In other examples, one or more echogenic features 133 may include recesses formed in shaft 101 via a secondary heat forming process such as branding or using a waffle iron on shaft 101. In some examples, echogenic features 133 may include a coil, such as a metal wire coil or a coil of any other suitable material, extending around the radially-outer surface, relative to longitudinal axis 135, of shaft 101. In some examples, shaft 101 may include a combination of recesses in the radially-outer surface of shaft 101 and a coil extending around the radially-outer surface, relative to longitudinal axis 135, of shaft 101. Echogenic features 133 may create an external radius of curvature on the radially-outer surface, relative to longitudinal axis 135, of shaft 101, which may facilitate positioning a portion of the radially-outer surface of shaft 101 normal relative to an endoscopic transducer. Echogenic features 133 may facilitate varying the angles of reflection of an ultrasound signal and may allow the ultrasound signal to be reflected back towards an endoscopic ultrasound transducer during operation.

Distal end portion 102 of medical device 100 may also include an expandable member 120. Expandable member 120 may extend circumferentially around the radially-outer surface, relative to axis 135, of shaft 101 and may be fixedly coupled to shaft 101 at its distalmost end 122 and at its proximalmost end 124. Expandable member 120 may be generally cylindrical and adjacent to the radially-outer surface, relative to axis 135, of shaft 101 when in a retracted state. Expandable member 120 may be expanded radially-outward, relative to axis 135, and may form a curved protrusion from shaft 101. Expandable member 120 may be fluidically connected to a fluid lumen 119, and expandable member 120 may be expanded by moving fluid into expandable member 120 via fluid lumen 119. Fluid lumen 119 may extend longitudinally through shaft 101 and may be fluidically connected to a fluid source at a proximal portion of medical device 100. In some examples, expandable member 120 may be a balloon, either compliant or noncompliant. Expandable member 120 may be configured to conform to radially-inward facing surfaces of a body lumen to form a seal between expandable member 120 and walls of the body lumen 104, for example to prevent movement of material 108 (such as tissue, stones, slug, or other debris) through body lumen 104 past expandable member 120. For example, material 108 may be prevented from moving proximally through body lumen 104 by expandable member 120 since expandable member 120 may form a seal with the radially-inward facing surface (or walls) of body lumen 104. The exterior surface of expandable member 120 may be smooth, may be configured to be atraumatic, and may be configured to slide across the walls of body lumen 104 when expandable member 120 is in an expanded state. While expandable member 120 is shown with a circular shape when in an expanded configuration (shown in FIG. 1), expandable member 120 is not so limited and may expand into any suitable shape to seal body lumen 104 and prevent movement of material 108 proximally through body lumen 104. In some examples, when fluid is removed from expandable member 120, such as when suction is applied to fluid lumen 119 to remove fluid from within expandable member 120, expandable member may be configured to retract and move into a position where expandable member 120 is adjacent to the radially-outer surface of shaft 101. For example, expandable member 120 may be made of an elastic material.

Distal end portion 102 may include a curved distalmost tip 136 configured to be atraumatic. In other examples, distalmost tip 136 may not be curved and may be any suitable shape. Distal end portion 102 may also include one or more fluid jet lumens 110, 112, 114. In some examples, all of lumens 110, 112, 114 may be connected to a single fluid lumen extending longitudinally through shaft 101. Lumens 110, 112, 114 may be configured to propel fluid out of the distal end of medical device 100. In some examples, lumens 110, 112, 114 may be configured to emit fluid from distal portion 102 at an angle relative to axis 135. In some examples, lumens 110, 112, 114 may be configured to emit fluid outward from medical device 100 in a plurality of directions that are angled relative to axis 135. For example, fluid emitted from lumens 110, 112, 114 may form a cone shape 126 shown in dotted lines in FIG. 1. Emitting fluid at an angle towards the wall of body lumen 104 may promote dislodgement of material 108 from body lumen 104. In some examples, lumens 110, 112, 114 may emit saline or specific enzymes configured to break apart tissue (e.g. stones), such as cholesterase enzymes. In other examples, fluid lumens 110, 112, 114 may be configured to release foam to facilitate coating walls of body lumen 104. In some examples, fluid lumens 110, 112, 114 may be configured to induce bubbles to fluid in order to facilitate duct structure visualization using ultrasound imaging techniques. For example, to induce foam or bubbles in a fluid spray, one of fluid lumens 110, 112, 114 may be configured to receive a gas, and the gas may then be combined in a small internal reservoir or intersection with another fluid lumen 110, 112, 114 (not shown) with a liquid solution of another fluid lumen 110, 112, 114. This combination of gas/liquid would then spray out of one or more openings of fluid lumens 110, 112, 114 to generate foam or an aerated solution.

Figure 2:
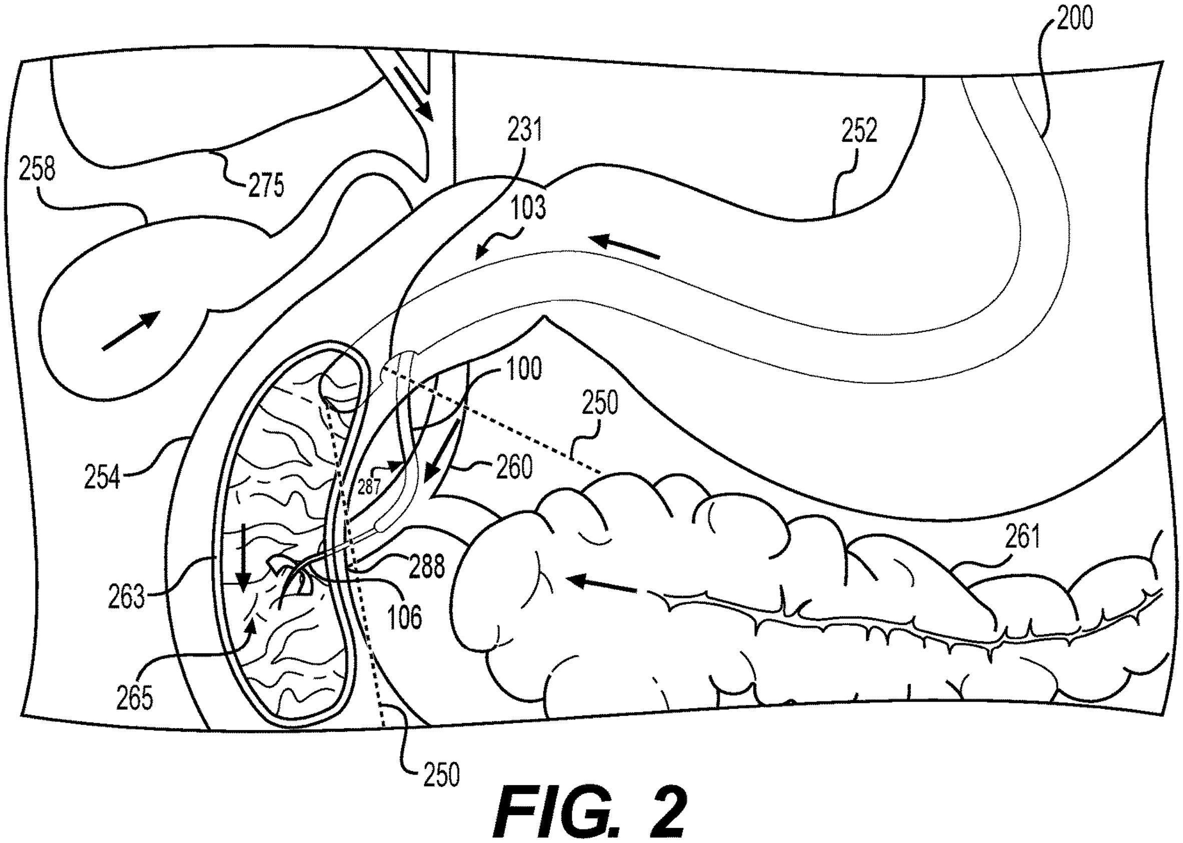
FIG. 2 is a perspective view of portions of a body of a patient and a distal end of the exemplary medical device system of FIG. 1, according to aspects of this disclosure.

FIG. 2 illustrates medical device system 103 positioned within a body of a patient. The portion of the body shown in FIG. 2 includes portions of the pancreaticobiliary system including pancreas 261, liver 275, stomach 252, gallbladder 258, duodenum 254 (an upper part of the small intestine immediately downstream of the stomach), and common bile duct 260. The direction of fluid flow (the downstream direction) of the pancreaticobiliary system is shown via straight arrows throughout FIG. 2. The common bile duct 260 and the pancreatic duct provide drainage from the liver 275, gallbladder 258, and pancreas 261 into duodenum 254. In some cases, common bile duct 260 may become obstructed as a result of cysts, enlarged lymph nodes, gallstones, inflammation, stricture, or narrowing of the duct from scarring, injury from surgery, tumors, or other causes, which can lead to inadequate drainage of bile and other material through the common bile duct 260. Medical device system 103 may facilitate removing material from the common bile duct 260 to improve drainage from the common bile duct 260. Some features of medical device 100 are omitted in FIG. 2 purely for ease of illustration, and medical device 100 in FIG. 2 includes all of the attributes shown in FIG. 1.

In operation, medical device system 103 may include medical device 100, guidewire 106, and an insertion device such as endoscope 200 shown in FIG. 2. A user, who may be a doctor, nurse, physician's assistant, or any other healthcare professional, may first position a guidewire 106 within the body of the patient through the stomach 252, the duodenum 254, and common bile duct 260. Specifically, guidewire 106 may extend through an opening made in a wall of duodenum 254 and into an opening 287 made in a wall of common bile duct 260 proximal from the distal end 288 of bile duct 260 (e.g. proximal from the ampulla of Vater), through common bile duct 260, and into duodenum 254. By positioning guidewire 106 in opening 287, bile duct 260, and duodenum 254, medical device 100 may access common bile duct 260 from an antegrade access point and move through common bile duct 260 in the same direction as fluid flow through common bile duct 260 when medical device 100 moves distally along guidewire 106. Moving medical device 100 through common bile duct 260 in the same direction as fluid flow may facilitate removal of debris from common bile duct 260 because debris may be pushed, via one or more fluid jets of medical device 100, in the same direction as fluid flow.

Once guidewire 106 is positioned within opening 287, common bile duct 260, and duodenum 254, a user may position endoscope 200 within duodenum 254 by positioning guidewire 106 within a working channel 231 of endoscope 200, and moving endoscope 200 distally along guidewire 106 through stomach 252 and duodenum 254. In some examples, guidewire 106 may already be positioned within working channel 231 prior to and during the positioning of guidewire 106 within opening 287. The direction of movement of endoscope 200 may be guided by guidewire 106. Throughout the procedure, the user may apply an ultrasound signal 250 via a transducer in endoscope 200 to visualize medical device 100 through one or more organ walls. The user may monitor the position of medical device 100 via ultrasound imaging.

Once endoscope 200 is positioned within duodenum 254 proximate to common bile duct 260, the user may then move medical device 100 through working channel 231 with guidewire 106 positioned within working channel 118 of medical device 100. When the user moves medical device 100 distally out of working channel 231, medical device 100 may move along guidewire 106 to travel out of duodenum 254, through opening 287, and into common bile duct 260. The user may then expand/inflate expandable member 120, for example via applying fluid flow to fluid lumen 119 to fill expandable member 120 with fluid. By expanding expandable member 120, medical device 100 may form a seal with the inner wall of common bile duct 260 to prevent movement of debris proximally or upstream in the common bile duct 260. For example, the formed seal of medical device 100 may prevent movement of debris proximally to opening 287. The user may then apply fluid to fluid lumens 110, 112, 114 to project fluid at the inner walls and with the lumen of common bile duct 260.

When expandable member 120 is in an expanded state, expandable member 120 may serve as an anchor coupling distal portion 102 of medical device 100 to common bile duct 260, which may facilitate maintaining a stable position of medical device 100 while applying fluid from fluid lumens 110, 112, 114 to common bile duct 260. Also, by expanding expandable member 120 into an expanded state, medical device 100 may be prevented from migrating into smaller duct branches during a procedure. Fluid projected from fluid lumens 110, 112, 114 may dislodge debris from the walls of common bile duct 260 and move debris downstream towards duodenum 254. The user may then push medical device distally (e.g. downstream) while expandable member 120 is in an expanded state, and radially-outer portions of expandable member 120 may remain in contact with inner walls of common bile duct 260 as medical device 100 moves distally, effectively sliding across the inner walls of common bile duct 260. After clearing or flushing debris (such as material 108) from common bile duct 260, the user may then release expandable member 120 from contacting inner walls of common bile duct 260, by deflating expandable member 120. The user may then remove medical device 100, endoscope 200, and guidewire 106 from the body of the patient.

Figure 3A:
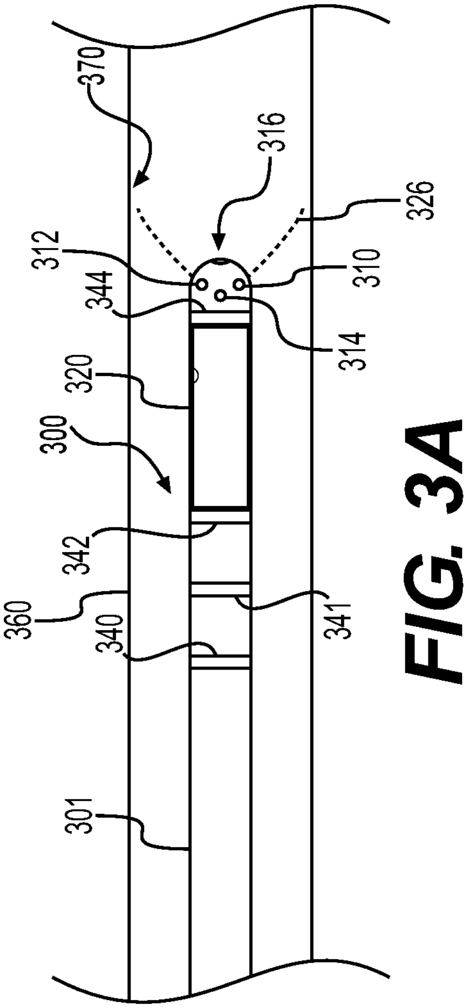
FIGS. 3A and 3B are side views of a portion of the exemplary medical device within a body lumen, according to aspects of this disclosure.
Figure 3B:
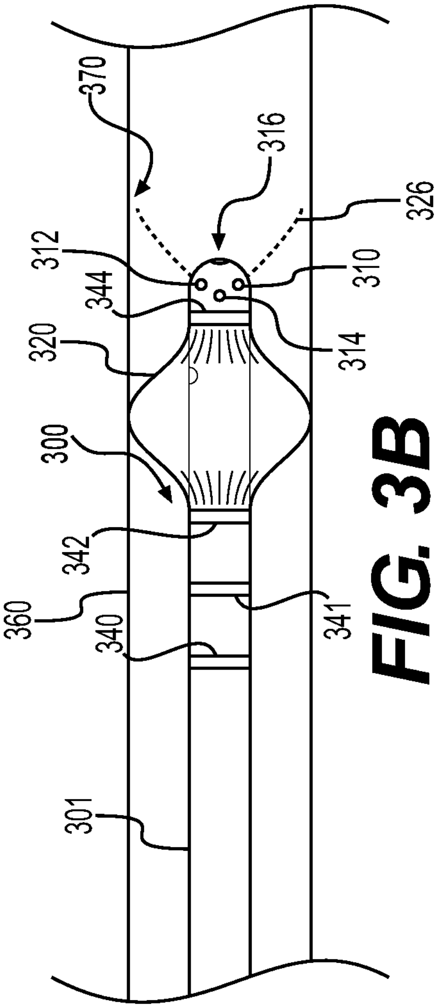

FIGS. 3A and 3B illustrate an alternative embodiment of medical device 300 positioned within a body lumen 360. Medical device 300 may include any of the features of medical device 100 described herein. Medical device 300 may include shaft 301, echogenic features 341-344, expandable member 320, fluid lumens 310, 312, 314, and working channel 316. In medical device 300, echogenic features 341-344 are spaced longitudinally from each other. Echogenic features 341-343 are positioned proximal from expandable member 320, and echogenic feature 344 is positioned distal from expandable member 320. Fluid lumens 310, 312, 314 emit fluid 326 radially-outward from a longitudinal axis of medical device 300, towards inner wall 370 of body lumen 360. FIG. 3A illustrates expandable member 320 in a retracted state. In some examples, expandable member 320 may contact shaft 301 the entire length of expandable member 120. FIG. 3B illustrates expandable member 320 in an expanded state, with a portion of expandable member 320 spaced from shaft 301 and a portion of expandable member 320 in contact with inner surface 370 of body lumen 360. Since expandable member 320 expands radially-outward from shaft 301 in all directions, expandable member 320 may form a seal with body lumen 360 and prevent debris from moving past expandable member 320 in body lumen 360. In an expanded state, expandable member 320 may brace medical device 300 to body lumen 360 and prevent movement of medical device 300 towards inner surface 370 of body lumen 360.

Figure 4:
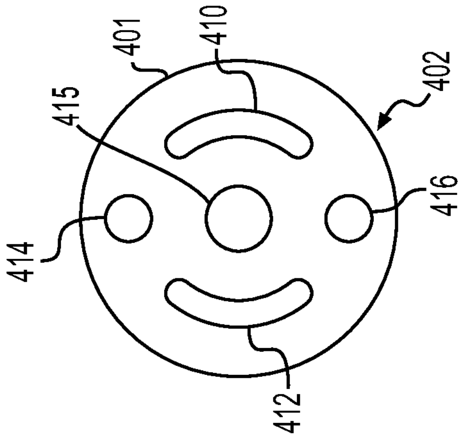
FIG. 4 is a front view of the distal end of an exemplary medical device, according to aspects of this disclosure.

FIG. 4 illustrates an alternative distal end 402 of a medical device 401. Medical device 401 may have any of the features of medical device 100 described herein. Medical device 401 may include working channel 415 extending longitudinally through medical device 401, and fluid lumen openings 410, 412, 414, 416. Fluid lumen openings 414, 416 may be circular, and fluid lumen openings 410, 412 may be oval shaped, may be arcuate, and may be concave towards working channel 416. Fluid lumen openings 410, 412 may emit fluid jets wider than fluid lumen openings 414, 416, which may facilitate removal of debris from the inner wall of common bile duct 260.

Figure 6:
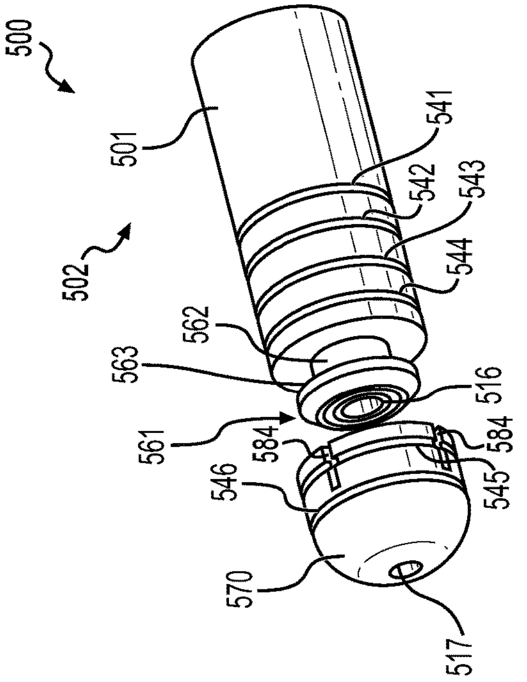
FIG. 6 is a perspective view of a distal end portion of an exemplary medical device with a distal end cap removed, according to aspects of this disclosure.
Figure 5:
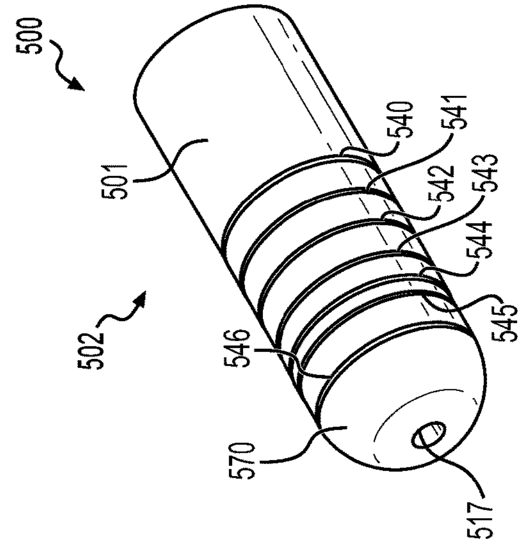
FIG. 5 is a perspective view of a distal end portion of an exemplary medical device, according to aspects of this disclosure.

FIG. 5 illustrates a distal portion 502 of an alternative embodiment of a medical device 500. Medical device 500 may have any of the features of any of the medical devices 100, 300 described herein. Medical device 500 may include shaft 501, echogenic features 540-545, working channel 517, and cap 570. As shown in FIG. 6, cap 570 may be removable, may include one or more echogenic features 545, 546, and may be coupled to shaft 501 at protrusion 562 and flange 563 of shaft 501. Protrusion 562 may extend distally from shaft 501, and flange 563 may extend radially outward, relative to axis 599, from protrusion 562. In some examples, flange 563 may include a beveled edge portion 561 extending circumferentially around flange 563, and beveled edge portion 561 may facilitate coupling cap 570 to shaft 501. Working channel 517 of cap 570 may be aligned with working channel 516 of shaft 501 when cap 570 is coupled to shaft 501. Cap 570 may be configured to rotate about central longitudinal axis 599 of shaft 501, when cap 570 is coupled to shaft 501. Slots 584 at a proximal end portion of cap 570 may facilitate coupling cap 570 to shaft 501, for example by allow a proximal portion of cap 570 to bend radially outward to allow cap 570 to receive flange 563.

Figure 7:
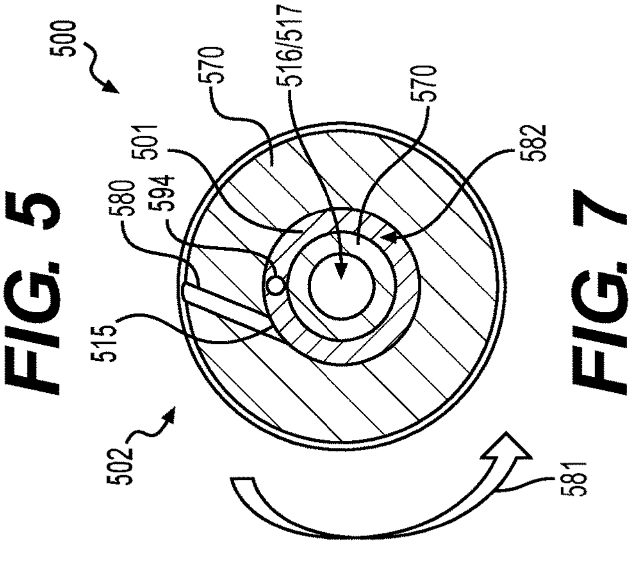
FIG. 7 is a front, cross-sectional view of the exemplary medical device of FIG. 5, according to aspects of this disclosure.

FIG. 7 illustrates a front, cross-sectional view of cap 570 coupled to shaft 501. As shown in FIG. 7, working channel 517 aligns with working channel 516 when cap 570 is coupled to shaft 501. Cap 570 may include a circular channel 582 configured to receive fluid from a fluid lumen 514 of shaft 501. Circular channel 582 may be fluidically connected with a side jet channel 580. Side jet channel 580 may extend from circular channel 582 to the exterior surface of cap 570. Side jet channel 580 may extend at an angle relative to circular channel 582.

Figure 8:
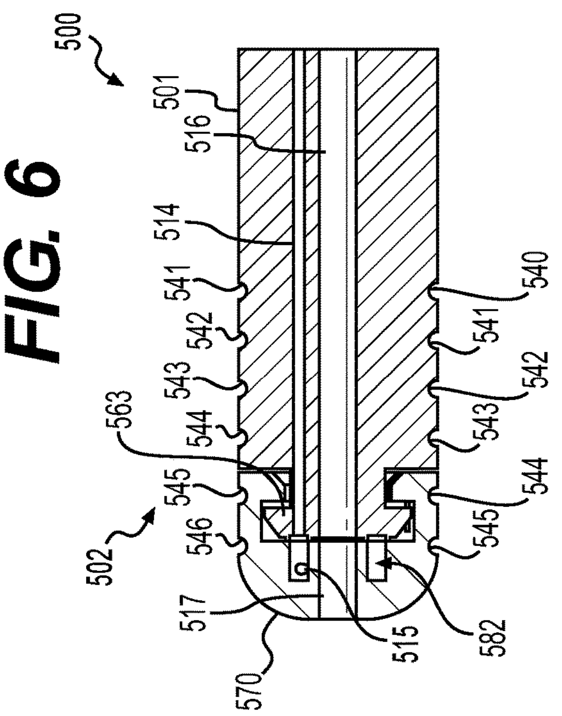
FIG. 8 is a side, cross-sectional view of the exemplary medical device of FIG. 5, according to aspects of this disclosure.

FIG. 8 illustrates a side, cross-sectional view of distal portion 502 of medical device 500 with cap 570 coupled to shaft 501. A fluid lumen 514 may extend longitudinally through shaft 501 and protrusion 563, and opening 594 (shown in FIG. 7) of fluid lumen 514 may be aligned with channel 582 when cap is coupled to shaft 501. A circular flange 595 of cap 570 may extend radially inward towards working channel 517/working channel 516, and circular flange 595 may extend between flange 563 and a distal end face 596 of shaft 501. In some examples, circular flange 595 may include a chamfer to facilitate coupling cap 570 to shaft 501, e.g. by facilitating radially expanding the proximal portion of cap 570 when a user pushes cap 570 onto protrusion 562. A seal may be formed between a distalmost end of protrusion 562/flange 563 and cap 570 such that fluid is prevented from moving out of circular channel 582 except for through side jet channel 580. Circular flange 595 may prevent cap 570 from moving distally relative to shaft 501 during operation.

When fluid is supplied to fluid lumen 514, fluid may flow out of fluid lumen 514 into circular channel 582 and through side jet channel 580. Opening 515 of side jet channel 580 allows fluid to flow from circular channel 582 into side jet channel 580. Since side jet channel 582 is angled relative to circular channel 582, the force of fluid flowing through side jet channel 582 may cause cap 570 to rotate relative to shaft 501 about axis 599. As shown via arrow 581 in FIG. 7, cap 570 may rotate counter-clockwise when fluid flows through circular channel 582 and side jet channel 580. Since cap 570 is rotated by the power of fluid flowing through circular channel 582 and side jet channel 580, cap 570 ejects fluid from side jet channel 580 in all directions radially outward from axis 599. Cap 570 may provide a sprinkler effect by propelling fluid outward from side jet channel 580. By providing rotating cap 570 in medical device 500, medical device 500 does not require multiple fluid lumens.

Figure 9A:
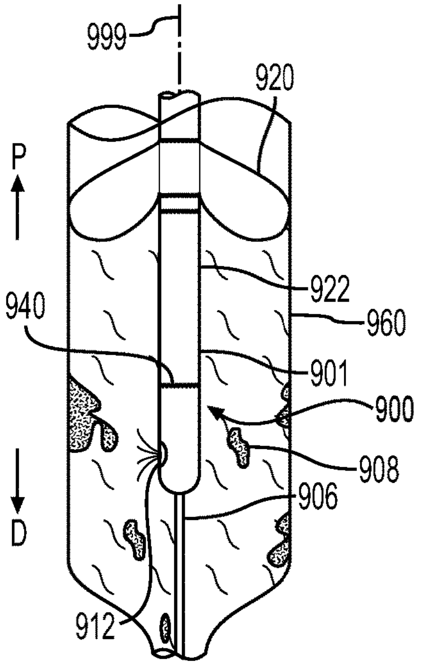
FIGS. 9A and 9B are side views of a distal portion of an exemplary medical device system within a body lumen, according to aspects of this disclosure.
Figure 9B:
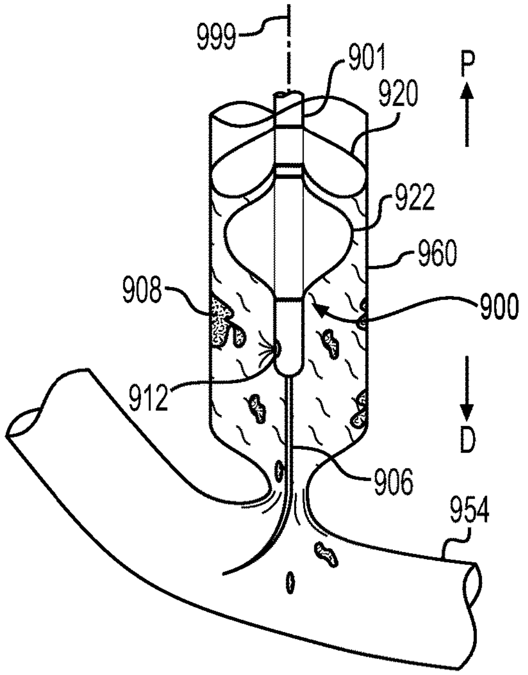

FIGS. 9A and 9B illustrate an alternative embodiment of a medical device 900 positioned within body lumen 960, with guidewire 906 positioned within a working channel of medical device 900. Medical device 900 may include shaft 901, expandable members 920, 922, fluid lumen 912, and working channel 917. Medical device 900 may include any of the features described herein with regard to medical devices 100, 300, 500. Expandable member 920 may be positioned proximal from expandable member 922, and expandable member 920 may be conical when in an expanded state. FIG. 9A shows expandable member 920 in an expanded state, and expandable member 922 in a retracted state. As shown in FIG. 9A, expandable member 920 may extend radially outward from central longitudinal axis 999 of shaft 901 and may be angled relative to axis 999 such that the radially-outermost portions of expandable member 920 are distal relative to the radially-innermost portions of expandable member 920. Since expandable member 920 is conically shaped and angled relative to axis 999, filling body lumen 960 with fluid may push expandable member 920 proximally and further radially-outward from axis 999, and thus may increase the pressure applied by expandable member 920 on body lumen 960. By increasing pressure applied by expandable member 920 on body lumen 960, medical device 900 may be held in position even while pressure is being applied to medical device 900 from fluid filling body lumen 960 distal from expandable member 920. Expandable member 922 may be positioned adjacent to expandable member 920, and expandable member 922 may expand uniformly radially-outward from axis 999. In some examples, expandable member 922 may be configured to abut (contact) expandable member 920 when each of expandable member 920 and expandable member 922 are in an expanded state.

In operation, after positioning medical device 900 within body lumen 960, a user may first expand expandable member 920. In some examples, the user may expand expandable member 920 to a position in which expandable member 920 abuts body lumen 960 and may form a seal around the inner wall 970 of body lumen 960. When expandable member 920 is in an expanded state (shown in FIGS. 9A and 9B), fluid may be prevented from moving proximally through body lumen 960 past expandable member 920. Once expandable member 920 is in an expanded state, the user may then move fluid into body lumen 960 from fluid lumen 912, such as by actuating an actuator at a proximal portion of medical device 900 to apply fluid to fluid lumen 912. In some examples, the user may move shaft 901 proximally or distally to distribute fluid from fluid lumen 912 throughout body lumen 960. After filling all or a portion of body lumen 960 distal from expandable member 920, the user may then facilitate movement of fluid within body lumen 960 to duodenum 954 by expanding expandable member 922. By expanding expandable member 922 while expandable member 920 is in an expanded state, fluid may be pushed distally through body lumen 960 and into duodenum 954. Also, expanding expandable member 922 while expandable member 920 is in an expanded state may facilitate movement of material 908 (e.g. debris, tissue, stones, etc.) out of body lumen 960 and into duodenum 954. In some examples, the user may push medical device 900 distally to aid in moving fluid and material 908 distally through body lumen 960. A user may then retract expandable member 922, which may release pressure within body lumen 960 created from both expandable member 920 and expandable member 922. After retracting expandable member 922, the user may then retract expandable member 920, move medical device 900 distally through body lumen 960, and repeat the above-described steps, if necessary to remove additional material 908 from lumen 960. The user may then remove medical device 900 from the body of the patient.

Figure 10:
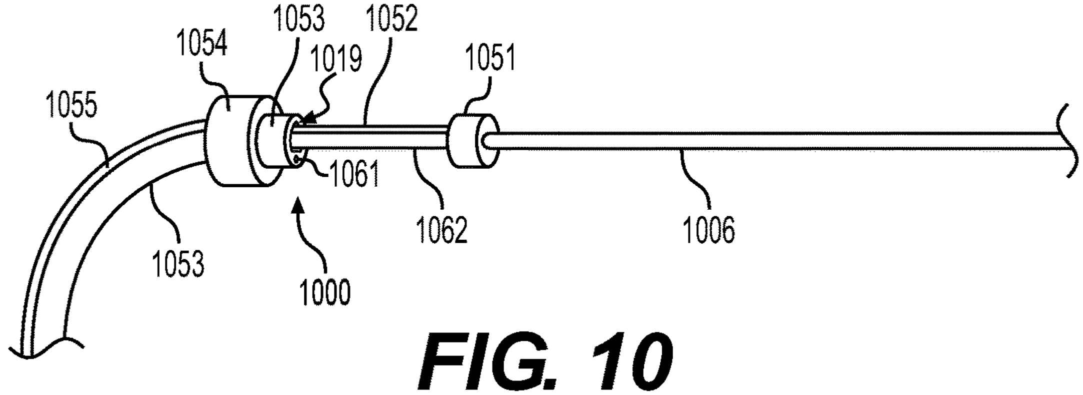
FIG. 10 is a side view of a portion of a medical device system, according to aspects of this disclosure.
Figure 11:
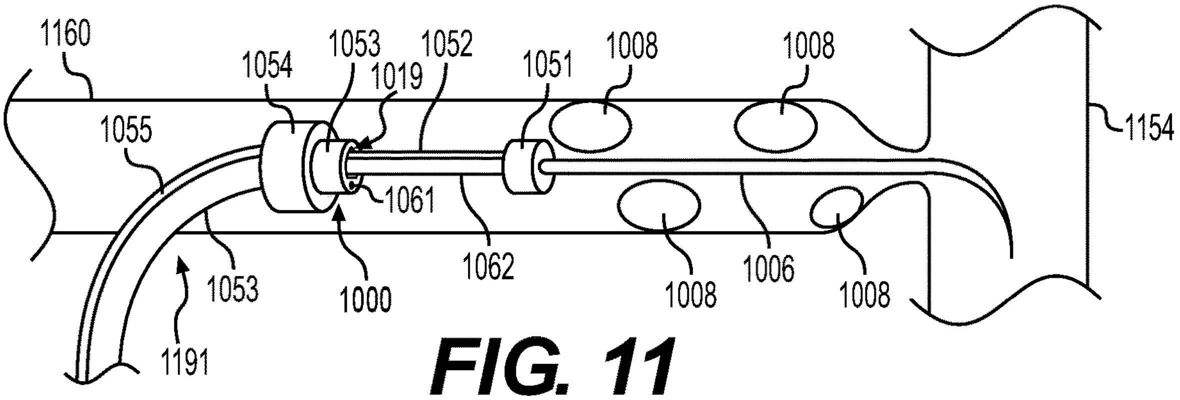
FIG. 11 is a side view of the medical device system of FIG. 10 within a body lumen, according to aspects of this disclosure.

FIG. 10 shows a distal portion of an alternative embodiment of a medical device 1000 for removing debris from a body lumen 1160. Medical device 1000 may have any of the features described herein related to any of the other medical devices 100, 300, 500, 900. Medical device 1000 may include a main shaft 1053 extending longitudinally to an expandable member 1054 and a distal end 1053' of main shaft 1053. Expandable member 1054 may extending circumferentially around main shaft 1053 and be positioned proximate to distal end 1053' of main shaft 1053. Fluid channel 1055 may extend longitudinally adjacent to main shaft 1053, may be integral with main shaft 1053, and/or may extend within main shaft 1053. Fluid channel 1055 may be fluidically coupled to expandable member 1054 and configured to supply fluid to expandable member 1054. Main shaft 1053 may include working channel 1019 extending longitudinally through main shaft 1053. Working channel 1019 may be configured to receive a plunger shaft 1062 and a fluid channel 1052 such that plunger shaft 1062 and fluid channel 1052 may move proximally and distally through working channel 1019. Main shaft 1053 may further include a fluid channel 1061 extending within main shaft 1053, and fluid channel 1061 may be configured to supply fluid to an area distal to expandable member 1054.

Plunger shaft 1062 may extending longitudinally through main shaft 1053 and out of distal end 1053' of main shaft 1053. A second expandable member 1051 may be coupled to a distal end of plunger shaft 1062. A working channel 1017 may extend longitudinally through plunger shaft 1062 and may be configured to receive a guidewire 1006. Fluid channel 1052 may extend longitudinally adjacent to plunger shaft 1062 and may be fluidically connected to second expandable member 1051. In other examples, fluid channel 1052 may be integral with plunger shaft 1062 and/or may be within plunger shaft 1062. In some examples, plunger shaft 1062, fluid channel 1052, and second expandable member 1051 may be configured to move through working channel 1019 when second expandable member 1051 is in a retracted state. Second expandable member 1051 may be configured to expand radially-outward from a central longitudinal axis 1099 of plunger shaft 1062. Expandable member 1054 may transition from a retracted state to an expanded state when fluid is suppled to expandable member 1054 from fluid channel 1055, and second expandable member 1051 may transition from a retracted state to an expanded state when fluid is suppled to second expandable member 1051 from fluid channel 1052.

Figure 12:
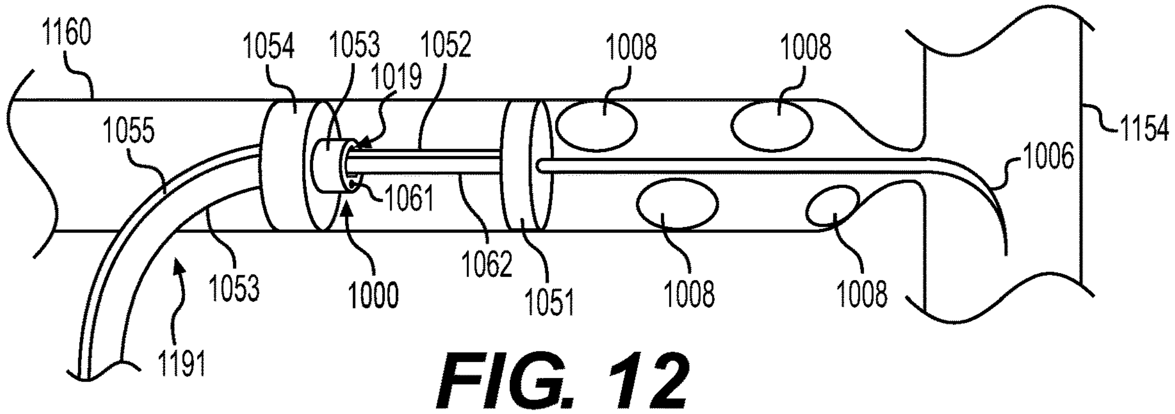
FIGS. 12-15 are side views of the exemplary medical device system of FIG. 10 within a body lumen, according to aspects of this disclosure.

FIGS. 11-15 illustrate an exemplary method for removing material from a body lumen 1160 using medical device 1000. A user may first position a guidewire 1006 within a target body lumen 1160, such as common bile duct 260. A user may then position guidewire 1006 within working channel 1017, and move medical device 1000 distally along guidewire 1006 and into target body lumen 1160. Once a distal portion of medical device 1000, including expandable members 1051, 1054 and distal end 1053', are positioned within body lumen 1160 (shown in FIG. 11), the user may then expand each of expandable members 1051, 1054. FIG. 12 shows both expandable members 1051, 1054 in an expanded state, with each of expandable members 1051, 1054 in contact with body lumen 1160. Each of expandable members 1051, 1054 may contact body lumen 1160 around a radially-outer surface of each expandable member 1051, 1054, relative to central longitudinal axis 1099, and may form a seal around a portion of, or the entire circumference of, body lumen 1160.

Figure 13:
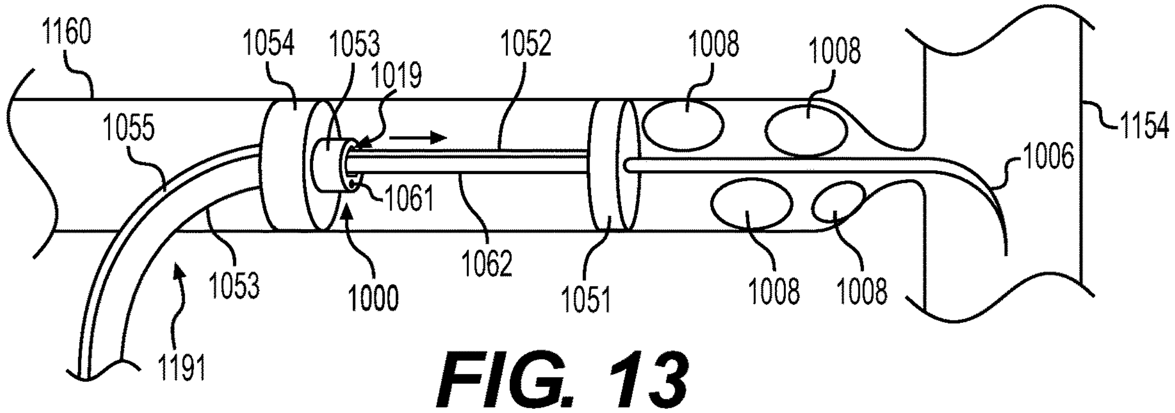
Figure 14:
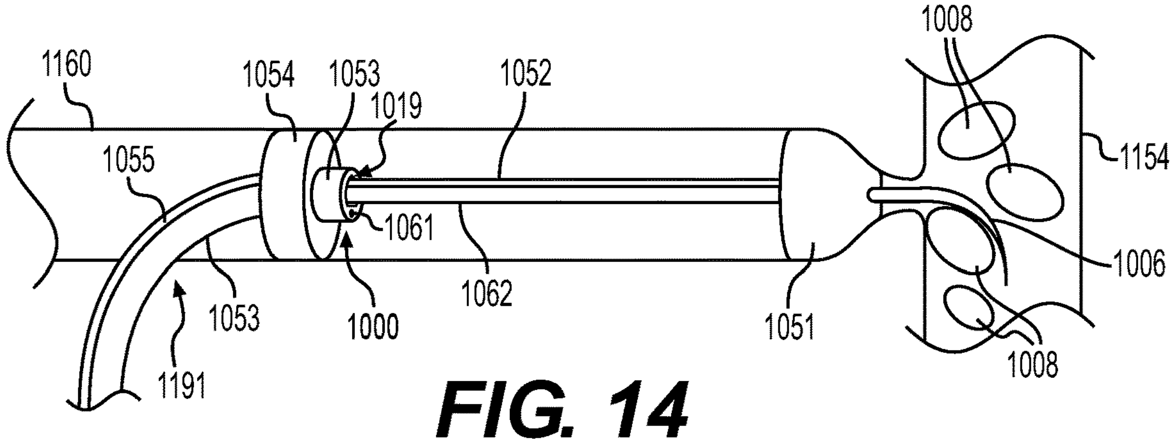
Figure 15:
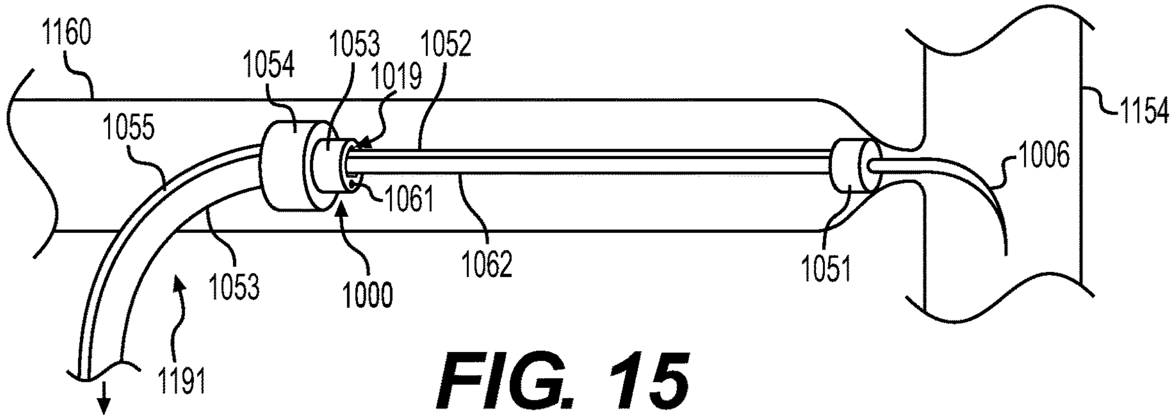

Once both expandable members 1051, 1054 are in an expanded state, the user may apply fluid to fluid channel 1061 to move fluid into a space within body lumen 1160 between expandable member 1051 and expandable member 1054. As fluid from fluid lumen 1061 collects within body lumen 1160, pressure may build within body lumen 1160 from the fluid in the space between expandable member 1051 and expandable member 1054, and this pressure may cause expandable member 1051 to move distally relative to expandable member 1054. FIGS. 13 and 14 show the distal movement of expandable member 1051 relative to expandable member 1054 as fluid channel 1061 continues to supple fluid to body lumen 1160. As expandable member 1051 moves distally, material 1008 within body lumen 1160 may be moved distally and may be pushed out of body lumen 1160, for example may be pushed into a larger body lumen 1154 (e.g. duodenum) connected to body lumen 1160. Expandable member and/or shaft 1053 may stay in place as expandable member 1051 and shaft 1062 moves distally, and in some examples expandable member 1054 may form a seal with body lumen 1160 to hold expandable member 1054 in place while expandable member 1051 moves distally. In some examples, expandable member 1051 may be stopped when expandable member 1051 reaches a narrower area 1088 (shown in FIG. 14) of body lumen 1160. Once a desired amount of debris 1008 has been cleared from body lumen 1160, the user may return expandable member 1051 to an unexpanded state and allow fluid collected between expandable member 1051 and expandable member 1054 to flow out of body lumen 1160. The user may then return expandable member 1054 to an unexpanded state, and remove medical device 1000 from the body of the patient.

Each of the aforementioned devices and systems may be used to visualize, manipulate, clean, flush, and/or otherwise move bodily material. Any of the aforementioned devices may be used with an insertion device, such as an endoscope or duodenoscope, equipped with ultrasonic imaging capabilities. In any of the aforementioned methods, a user may view the one or more medical devices using ultrasound imaging techniques and may be used to clear bile, slug, or other material from a common bile duct of a patient.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A method for removing a material from a body lumen, the method comprising:

positioning a first medical device within the body lumen;

expanding a first expandable member at a distal portion of the first medical device so that the first expandable member abuts a wall of the body lumen;

expanding a second expandable member, wherein the second expandable member is distal of the first expandable member; and after expanding the second expandable member, delivering a fluid from a fluid lumen of the first medical device into a portion of the body lumen that is between a distalmost end of the first expandable member and a proximalmost end of the second expandable member, wherein a pressure of the fluid between the first expandable member and the second expandable member causes the second expandable member to move distally relative to the first expandable member, wherein such distal movement of the second expandable member removes the material from the body lumen.

2. The method of claim 1, wherein the fluid is delivered from the fluid lumen via a first, oval shaped opening and a second, circular opening.

3. The method of claim 1, wherein the first medical device includes at least one echogenic feature.

4. The method of claim 3, further comprising:
positioning a guidewire within the body lumen; and
moving the first medical device along the guidewire.

5. The method of claim 1, wherein expanding the first expandable member expands the first expandable member radially outward relative to a central longitudinal axis of the first medical device.

6. The method of claim 1, wherein the first expandable member is angled relative to a central longitudinal axis of the first medical device after the first expandable member is expanded, and wherein a radially-outermost portion of the first expandable member is distal to a radially-innermost portion of the first expandable member after the first expandable member is expanded.

7. The method of claim 1, further comprising:
applying an ultrasound signal to the first medical device from a second medical device, wherein the second medical device is positioned outside of the body lumen.

8. The method of claim 1, wherein the first expandable member and the second expandable member each forms a seal with the body lumen after the first expandable member and the second expandable member have been expanded.

9. The method of claim 1, wherein a distal opening of the fluid lumen is positioned between the first expandable member and the second expandable member.

10. The method of claim 1, wherein the body lumen is a common bile duct of a patient, and wherein positioning the first medical device includes entering the common bile duct via an opening made in the common bile duct.

11. A method for removing a material from a body lumen, the method comprising:
positioning a medical device within the body lumen;
expanding a proximal expandable member of the medical device;
expanding a distal expandable member of the medical device; and
with the proximal expandable member and the distal expandable member expanded, delivering a fluid from an opening in the medical device into a gap between the proximal expandable member and the distal expandable member, wherein the fluid contacts and exerts a pressure on the distal expandable member, thereby causing the distal expandable member to move distally relative to the proximal expandable member, wherein the fluid contacts the proximal expandable member, the distal expandable member, and a wall of the body lumen.

12. The method of claim 11, further comprising:
using the distal expandable member to push the material that is distal of the distal expandable member in a distal direction.

13. The method of claim 11, wherein the opening is in a shaft of the medical device, wherein the opening is distal to the proximal expandable member and proximal of the distal expandable member.

14. The method of claim 13, wherein the shaft is a first shaft, wherein the proximal expandable member is coupled to the first shaft, wherein the distal expandable member is coupled to a second shaft.

15. The method of claim 14, wherein the opening is formed in a distalmost face of the first shaft.

* * * * *